United States Patent [19]

Kleiner

[11] Patent Number: 4,626,386
[45] Date of Patent: Dec. 2, 1986

[54] PROCESS FOR THE PREPARATION OF ALKALI METAL AND ALKALINE EARTH METAL SALTS OF DIARYLPHOSPHINIC ACIDS

[75] Inventor: Hans-Jerg Kleiner, Kronberg, Fed. Rep. of Germany

[73] Assignee: Hoechst Aktiengesellschaft, Frankfurt am Main, Fed. Rep. of Germany

[21] Appl. No.: 725,131

[22] Filed: Apr. 19, 1985

[30] Foreign Application Priority Data

Apr. 21, 1984 [DE] Fed. Rep. of Germany ....... 3415070

[51] Int. Cl.$^4$ ................................................ C07F 9/30
[52] U.S. Cl. .............................. 260/502.4 R; 585/469
[58] Field of Search .................................. 260/502.4 F

[56] References Cited

FOREIGN PATENT DOCUMENTS 1044813 5/1959 Fed. Rep. of Germany .

OTHER PUBLICATIONS

Merck Index, 6th Ed. (1952), p. 778.
Aldrich, Catalog Handbook of Fine Chemicals, 1984–1985, p. 921.

Primary Examiner—J. E. Evans
Attorney, Agent, or Firm—Curtis, Morris & Safford

[57] ABSTRACT

The alkali metal and alkaline earth metal salts of diarylphosphinic acids are prepared by reacting triarylphosphane oxides with alkali metal or alkaline earth metal hydroxides in a molar ratio of about 1:1 or 0.5, in the presence of water, under elevated pressure and at elevated temperature. In this manner, the alkali metal or alkaline earth metal salts of diphenylphosphinic acid are formed from triphenylphosphane oxide, which is the preferably used triarylphosphane oxide.

Other salts or the corresponding free diarylphosphinic acids can, if desired, be obtained from the alkali metal and alkaline earth metal salts in a conventional manner. The products are principally intermediates in various fields.

8 Claims, No Drawings

PROCESS FOR THE PREPARATION OF ALKALI METAL AND ALKALINE EARTH METAL SALTS OF DIARYLPHOSPHINIC ACIDS

Diarylphosphinic acids are compounds of the general formula

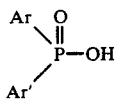

wherein Ar and Ar' are identical or different aromatic radicals; they are principally intermediates in various fields, such as, for example, the pharmaceutical and crop protection sectors.

Their alkali metal and alkaline earth metal salts, from which the free diarylphosphinic acids can be obtained in a conventional manner (for example by adding hydrochloric acid), are prepared, for example by the process described in DE-C No. 1,044,813, by fusing together triarylphosphane oxides or diaryl-aralkyl-phosphane oxides and alkali metal or alkaline earth metal hydroxides at temperatures in the range of about 210°–360° C. The reaction is based on the following equations (in the equations given here, the alkali metal hydroxide is NaOH and the alkaline earth metal hydroxide is Ca(OH)$_2$):

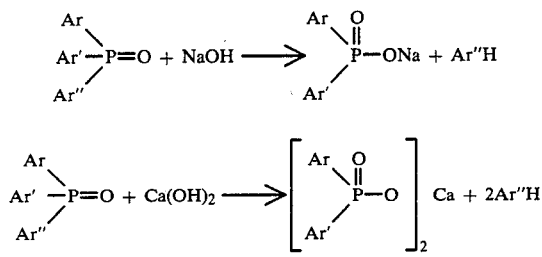

In the formulae, Ar and Ar' again denote identical or different aromatic radicals, and Ar" is an aromatic or aralkyl radical.

Among the three organic radicals of the starting phosphane oxide, the one which is preferably eliminated in this case is that which, as an anion, possesses the greatest resonance stabilization, for example the benzyl radical before the phenyl radical; cf. column 3, lines 27 to 30 of the abovementioned DE-C patent.

As shown in the equations, one mole of alkali metal hydroxide or half a mole of alkaline earth metal hydroxide is required per mole of starting phosphane oxide, according to the stoichiometry of the reaction. In the abovementioned DE-C patent, however, the use of excess alkali metal or alkaline earth metal hydroxide is described as being "advantageous". In all of the examples in the DE-C, with one exception, the alkali metal or alkaline earth metal hydroxide was used in excess, in some cases in a substantial excess. Only in one example (Example 5b) was the stoichiometric (equimolar) amount of alkali metal hydroxide used; however, the phosphane oxide starting material for this example was not a triarylphosphane oxide but a diaryl-a ralkyl-phosphane oxide, i.e. diphenylbenzylphosphane oxide. Because the benzyl radical can be eliminated more readily (compared with the phenyl radical), elimination apparently takes place here to a satisfactory extent even without excess alkali metal hydroxide. On the other hand, however, the starting material (diphenylbenzylphosphane oxide) used in this example is less readily available than the triarylphosphane oxides, in particular those having three identical aryl radicals.

With regard to the reaction of the triarylphosphane oxides with an excess (over and above the stoichiometric amount) of alkali metal or alkaline earth metal hydroxides, another disadvantage, apart from the obvious necessity of using this hydroxide excess, is that the diarylphosphinic acid salts obtained by the process are solids under the reaction conditions, and considerable heat-transfer problems therefore arise in the case of industrial batches.

Another disadvantage arises in the working up of the reaction mixture. After cooling, the melt is first dissolved in water. Because of the excess alkali metal or alkaline earth metal hydroxide, the solution is then strongly alkaline. Obtaining pure alkali metal or alkaline earth metal phosphinates from this strongly alkaline solution is possible only with considerable effort, for example by careful fractional crystallization.

If, on the other hand, the intention is to obtain not the phosphinic acid salts but the free diarylphosphinic acid from the strongly alkaline solution, a substantial amount of a strong acid, such as, for example, hydrochloric acid, has to be added to the solution in order to effect neutralization. As a result of this, the diarylphosphinic acid is liberated; after isolation, which is carried out in the usual manner, the yield is said to be between 80 and 100% of theory. The substantial amounts of salts then have to be worked up in a manner which causes little pollution, by processes which are frequently rather expensive.

As our own experiments have shown, the disadvantages associated with the reaction of triarylphosphane oxides with excess alkali metal or alkaline earth metal hydroxides in the melt cannot, furthermore, be overcome in a simple manner by carrying out the reaction only with stoichiometric amounts of alkali metal or alkaline earth metal hydroxides. In such a procedure, in fact, only unsatisfactory yields (up to about 70% of theory) of the corresponding alkali metal or alkaline earth metal salts are obtained in reaction times which are in any way reasonable (up to about 8 hours).

In an attempt to improve the reaction disclosed in DE-C No. 1,044,813 in such a way that the disadvantages associated with the reaction are no longer present, it was found that this aim is achieved by reaction of triarylphosphane oxides with the stoichiometric amounts of alkali metal or alkaline earth metal hydroxides in the presence of water under elevated pressure.

The invention therefore relates to a process for the preparation of alkali metal and alkaline earth metal salts of diarylphosphinic acids by reacting triarylphosphane oxides with alkali metal or alkaline earth metal hydroxides at elevated temperature, wherein the reaction is carried out using a molar ratio of triarylphosphane oxide to alkali metal or alkaline earth metal hydroxide of about 1:1 or 0.5, in the presence of water under elevated pressure.

This procedure gives high—generally quantitative or virtually quantitative—yields of the corresponding phosphinic acid salts in reaction times which are not excessively long. Since no excess of alkali metal or alkaline earth metal hydroxide is required, the disadvantages associated with the use of the excess hydroxides according to the process of DE-C No. 1,044,813 do not arise in this case. Because of the presence of water during the reaction, the latter is easier to carry out; in particular, aqueous alkali metal or alkaline earth metal hydroxide solutions can be used. Since alkali metal or alkaline earth metal hydroxides are not used in excess, the reaction mixture is therefore also easier to work up; where it is desired to obtain the free diarylphosphinic acids, it is found, in particular, that the substantial amounts of salt which are disadvantageous for the process of DE-C No. 1,044,813 are not formed.

The success of the reaction when carried out in the manner according to the invention using stoichiometric amounts of alkali metal or alkaline earth metal hydroxides was extremely surprising, since, on the basis of our own experiments and because of the unfavorable result of the reaction of triarylphosphane oxides with stoichiometric amounts of alkali metal or alkaline earth metal hydroxides in the melt according to the process of DE-C No. 1,044,813, an improved result could hardly be expected without a substantial increase in the amount of alkali metal or alkaline earth metal hydroxide. The advantageous result nevertheless obtained is clearly attributable to the presence of water and the fact that the reaction is carried out under elevated pressure.

Starting triarylphosphane oxides suitable for the process are compounds which have either identical or different aryl radicals which in turn can be either substituted or unsubstituted. When the aryl radicals are substituted, the substituents should of course be inert in the reaction medium and under the reaction conditions, i.e. they should not react in an undesirable manner. Examples of aryl radicals are the phenyl and the naphthyl radicals, and examples of inert substituents are alkyl groups, alkoxy groups, amino groups, alkylamino groups and dialkylamino groups, preferred alkyl groups being those having up to 4 carbon atoms. Preferred triarylphosphane oxides are those having 3 identical aryl groups, in particular triphenylphosphane oxide.

The triarylphosphane oxides are obtainable in a conventional manner, for example by treating quaternary phosphonium salts with an alkali or by oxidation of tertiary phosphines, or by reacting phosphoric acid chlorides with Grignard reagents, and are, in some cases, also commercial products. Triphenylphosphane oxide is also obtained, in some cases in substantial amounts, as a by-product in industrial syntheses, such as, for example, the "Wittig reaction" (=reaction of aldehydes or ketones with triphenylphosphane-alkylenes, in particular with triphenylphosphane-methylene).

Virtually all hydroxides of the alkali metals (Li, Na, K, Rb and Cs) and alkaline earth metals (Be, Mg, Ca, Sr and Ba) can be used as alkali metal and alkaline earth metal hydroxides. NaOH, KOH and Ba(OH)$_2$ are preferably used.

The alkali metal and alkaline earth metal hydroxides are employed in approximately stoichiometric amounts, i.e. in a molar ratio of triarylphosphane oxide to alkali metal hydroxide of about 1:1, or of triarylphosphane oxide to alkaline earth metal hydroxide of about 1:0.5. Although the reaction also takes place in principle with excess alkali metal or alkaline earth metal hydroxide, this reduces the advantages of the procedure according to the invention (using an approximately stoichiometric molar ratio).

The amount of water which should be present during the reaction according to the invention can in principle vary within wide limits. However, an amount of water of about 10 to 100% by weight, in particular of about 20 to 60% by weight, relative to the weight of the triarylphosphane oxide employed, is preferred. This makes it possible to use aqueous alkali metal and alkaline earth metal hydroxide solutions.

The reaction is carried out under elevated pressure, preferably in a closed system under autogenous (elevated) pressure.

The reaction temperature is of the order of magnitude of the temperatures as stated for the process according to DE-C No. 1,044,813. The temperature range generally employed is between about 160° and 350° C., preferably between about 200° and 280° C.

It may be advantageous to carry out the reaction under an inert gas atmosphere, examples of suitable inert gases being nitrogen and argon.

The reaction time can vary within relatively wide limits, usually between about 1 and 30 hours; in general, however, high yields are obtained in only about 5 to 10 hours.

Both the continuous procedure and the batchwise procedure are possible.

To carry out the reaction, the triarylphosphane oxide, the alkali metal or alkaline earth metal hydroxide and the appropriate amount of water are heated in a pressure vessel to the desired reaction temperature, and left at this temperature for about 1 hour or longer. When the reaction is complete, the pressure vessel is opened and, if appropriate, further water is added. In general, two layers are then formed. The upper layer consists of an aromatic hydrocarbon—where the preferred starting material triphenylphosphane oxide is used, it consists of benzene—and the lower layer consists of an aqueous, virtually neutral solution of the alkali metal or alkaline earth metal salt of the diarylphosphinic acid, which may also contain relatively small amounts of aromatic hydrocarbon. After phase separation, the alkali metal or alkaline earth metal salts of the corresponding diarylphosphinic acid are finally obtained from the aqueous phase, for example, by distilling off the water or by spray-drying measures, in general in virtually quantitative yield and high purity. If desired, the salts can be converted in a conventional manner to other salts or to the particular free diarylphosphinic acid.

If the free diarylphosphinic acid is desired, a strong inorganic acid, such as, for example, hydrochloric acid, can be added directly to the reaction mixture obtained when the reaction according to the invention is complete, advantageously in the presence of an organic solvent, such as, for example, chlorobenzene, which readily dissolves the diarylphosphinic acid at about 100° C. In this procedure, the free diarylphosphinic acid formed, together with the aromatic hydrocarbon present in the reaction mixture, is dissolved in the organic solvent at about 100° C. When the aqueous layer has been separated off and, if required, the organic layer has been filtered, the diarylphosphinic acid is precipitated in crystalline form from the organic layer on cooling.

The invention is illustrated in detail by the examples below. The examples (according to the invention) are followed by a comparative example which shows that the reaction of triphenylphosphane oxide with an equimolar amount of alkali metal hydroxide in the melt according to the process of DE-C No. 1,044,813 gives only an unsatisfactory yield (about 70% of theory) of the diphenylphosphinic acid salt after about 8 hours. Towards the end of the reaction, which lasted about 8 hours, the reaction was so slow (detectable from the fact that elimination of benzene was now extremely slow) that, if necessary, a longer reaction time out of all proportion would have been required for a slight improvement in the yield.

EXAMPLE 1

278 g (=1 mole) of triphenylphosphane oxide, 40 g (=1 mole) of sodium hydroxide and 110 g of water were introduced into a 1 liter shaken nickel autoclave. The autoclave was then flushed with nitrogen and heated to 285° C. in the course of 3 hours. During this procedure, the pressure increased to 83 bar. The autoclave was kept at this temperature for a further 7 hours, after which it was cooled. 600 ml of water were added to the reaction mixture. The upper benzene layer was separated off. The lower aqueous layer contained the sodium salt of diphenylphosphinic acid. This solution was allowed to flow into a mixture of 500 ml of concentrated hydrochloric acid and 300 ml of water with vigorous stirring, diphenylphosphinic acid being precipitated. Filtration under suction and drying gave 216 g of product which was shown on the basis of a $^{31}$P-NMR spectrum to be free from organophosphorus impurities. This corresponded to a yield of 99% of theory.

EXAMPLE 2

278 g (=1 mole) of triphenylphosphane oxide, 56 g (=1 mole) of potassium hydroxide and 110 g of water were introduced into a 1 liter shaken nickel autoclave. The autoclave was then flushed with nitrogen and heated to 280° C. in the course of 2.5 hours. During this procedure, the pressure increased to 70 bar. The autoclave was kept at 285°–290° C. for a further 4 hours. The pressure increased to 72 bar during this time. The autoclave was then cooled. The upper (benzene) layer of the reaction mixture was separated off. The resulting neutral aqueous solution of the potassium salt of diphenylphosphinic acid was evaporated down in a vacuum from a water pump. After drying, 250 g of the potassium salt of diphenylphosphinic acid were obtained. This corresponded to a yield of 98% of theory.

EXAMPLE 3

278 g (=1 mole) of triphenylphosphane oxide, 160 g (=0.5 mole) of barium hydroxide 8-hydrate and 100 g of water were introduced into a 1 liter shaken nickel autoclave. The autoclave was then flushed with nitrogen and kept at 285° C. for 10 hours. During this procedure, the pressure increased to not more than 80 bar. The neutral reaction mixture which resulted after cooling, and which contained the barium salt of diphenylphosphinic acid, was mixed with 400 ml of water, 500 ml of concentrated hydrochloric acid and 2 liters of chlorobenzene, and the mixture was stirred for several hours at 95° C. Thereafter, the chlorobenzene layer was separated off while hot, filtered while hot, and cooled. After filtration under suction and drying, 175 g of diphenylphosphinic acid were obtained. This corresponded to a yield of 80% of theory.

EXAMPLE 4

278 g (=1 mole) of triphenylphosphane oxide, 40 g (=1 mole) of sodium hydroxide and 110 g of water were introduced into a 1 liter shaken nickel autoclave. The autoclave was then flushed with nitrogen and heated to 200° C. After about 30 hours, the reaction was completed under a pressure of 20 bar. After the reaction mixture had been cooled, about 800 ml of water were added. The upper benzene layer was then separated off at 45° C. The lower aqueous layer was further diluted with about 1 liter of water and then stirred at about 0° C. During this procedure, 36 g of triphenylphosphane oxide (=0.13 mole) were precipitated, and were filtered off under suction. The aqueous solution was then evaporated down, and the residue was allowed to flow into 500 ml of concentrated hydrochloric acid with vigorous stirring, diphenylphosphinic acid being precipitated. After filtration under suction and drying, 185 g of product were obtained. This corresponded to a yield of about 97.5% of theory at a conversion of 87%.

COMPARATIVE EXAMPLE 278 g (=1 mole) of triphenylphosphane oxide and 40 g (=1 mole) of finely powdered sodium hydroxide were mixed, and the stirred mixture was heated. At 160° C., the mixture was a readily stirrable melt. Above 205° C., benzene began to distill off and was collected in a vessel. A cold trap was also present downstream of the vessel. The temperature was increased with further continuous stirring, further benzene simultaneously being distilled off. After 30 minutes, the internal temperature had reached 250° C. At this point in time, some of the reaction mixture had already become a crystalline solid and could not be stirred, particularly at the walls of the reaction flask. After a further 2 hours, the internal temperature had reached 290° C. The contents of the flask had become solid and could not be stirred. The stirrer was therefore switched off in order to prevent it from being broken. After a total of 6.5 hours, 52 g of benzene had collected in the vessel. After a further hour with the internal temperature still at 290° C., only a further 1 g had collected in the vessel. The downstream cold trap was empty. After 7 hours (for 5 of which the temperature was 290° C.), a total of 53 g of benzene had formed. This corresponds to a yield of 68% of theory. The mixture was then cooled, and 400 ml of water were added. After prolonged stirring at 50° C., a clear aqueous solution was formed; this was allowed to run into a mixture of 500 ml of concentrated hydrochloric acid and 500 ml of water, with vigorous stirring and with cooling. After stirring had been continued for several hours, the product was filtered off under suction and washed with water. After drying, 230 g of product were obtained which, on the basis of the $^{31}$P-NMR spectrum, consisted of 28% of triphenylphosphane oxide and 72% of diphenylphosphinic acid.

I claim:

1. A process for the preparation of alkali metal and alkaline earth metal salts of diarylphosphinic acids by reacting triarylphosphane oxides with alkali metal or alkaline earth metal hydroxides at elevated temperature, wherein the reaction is carried out using a molar ratio of a triarylphosphane oxide to an alkali metal hydroxide of about 1:1 or a molar ratio of a triarylphosphane oxide to an alkaline earth metal hydroxide of about 1:0.5, wherein the reaction is carried out in the presence of water in an amount of about 10% or more by weight, relative to the weight of the starting triarylphosphane oxide, under elevated pressure.

2. The process as claimed in claim 1, wherein triphenylphosphane oxide is used as the triarylphosphane oxide.

3. The process as claimed in claim 1, wherein sodium hydroxide or potassium hydroxide is used as the alkali metal hydroxide, and barium hydroxide is used as the alkaline earth metal hydroxide.

4. The process as claimed in claim 1, wherein the reaction is carried out in the presence of an amount of water of about 10 to 100% by weight, relative to the weight of the starting triarylphosphane oxide.

5. The process as claimed in claim 1, wherein the reaction is carried out under autogenous pressure.

6. The process as claimed in claim 1, wherein the reaction is carried out at temperatures between about 160° and 350° C.

7. A process for the preparation of alkali metal and alkaline earth metal salts of diarylphosphinic acids by reacting triarylphosphane oxides with alkali metal or alkaline earth metal hydroxides at elevated temperature, wherein the reaction is carried out using a molar ratio of a triarylphosphane oxide to an alkali metal hydroxide of about 1:1 or a molar ratio of a triarylphosphane oxide to an alkaline earth metal hydroxide of about 1:0.5, wherein the reaction is carried out in the presence of water in an amount of about 20 to 60% by weight, relative to the weight of the starting triarylphosphane oxide, under elevated pressure.

8. The process as claimed in claim 1, wherein the reaction is carried out at a temperature between about 200° and 280° C.